(12) United States Patent
Castelli et al.

(10) Patent No.: US 8,022,048 B2
(45) Date of Patent: Sep. 20, 2011

(54) METHOD OF TREATING VITAMIN B12 DEFICIENCY

(75) Inventors: Cristina Castelli, New York, NY (US); Laura Kragie, Chevy Chase, MD (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 339 days.

(21) Appl. No.: 12/262,677

(22) Filed: Oct. 31, 2008
(Under 37 CFR 1.47)

(65) Prior Publication Data
US 2010/0016255 A1 Jan. 21, 2010

Related U.S. Application Data

(60) Provisional application No. 60/984,898, filed on Nov. 2, 2007, provisional application No. 61/020,108, filed on Jan. 9, 2008, provisional application No. 61/083,566, filed on Jul. 25, 2008.

(51) Int. Cl.
*A61K 31/70* (2006.01)
(52) U.S. Cl. ........................................ 514/52
(58) Field of Classification Search ........................ None
See application file for complete search history.

(56) References Cited

U.S. PATENT DOCUMENTS

| | | | |
|---|---|---|---|
| 5,650,386 | A | 7/1997 | Leone-Bay et al. |
| 5,665,379 | A | 9/1997 | Herslof et al. |
| 6,274,564 | B1 * | 8/2001 | Sarill et al. ...................... 514/52 |
| 7,169,776 | B2 | 1/2007 | Bernadino et al. |
| 7,456,215 | B2 | 11/2008 | Julian |
| 2005/0186267 | A1 | 8/2005 | Thompson et al. |
| 2006/0024241 | A1 | 2/2006 | Brown |
| 2006/0078623 | A1 | 4/2006 | Dhoot et al. |
| 2006/0116334 | A1 | 6/2006 | Hendrix |
| 2008/0234179 | A1 | 9/2008 | Li et al. |
| 2009/0143330 | A1 | 6/2009 | Levchik et al. |

OTHER PUBLICATIONS

Letter from Laura Kragie, M.D. addressed to Jay P. Lessler, Aug. 2, 2009.
Declaration of Cristina Castelli, Ph.D., dated Dec. 2, 2010 (3 pages).
U.S. Appl. No. 13/033,118, filed Feb. 23, 2011.
Andres, et al., The Syndrome of food-cobalamin malabsorption revisited in a department of internal medicine a monocentric cohort study of 80 patients. European Journal of Internal Medicine 14 (2003) 221-226.
Lane, et al., Treatment of vitamin B12-Deficiency Anemia: Oral Versus Parenteral Therapy, The Annals of Pharmacotherapy, Jul./Aug. 2002, vol. 36, 1268-1272; 1809-1810.
Adams, JF. The urinary excretion and tissue retention of cyanocobalamin by subjects given repeated parenteral doses. *J Clin Path* 1964; 17: 31-38.
Alani AW, Robinson JR. Mechanistic understanding of oral drug absorption enhancement of cromolyn sodium by an amino acid derivative. *Pharm Res.* 2008; 25: 48-54.
Andres E, Kurtz JE, Perrin AE, Maloisel F, Demangeat C, Goichot B, Schlienger JL. Oral cobalamin therapy for the treatment of patients with food-cobalamin malabsorption. *Am J Med* 2001; 111: 126-9.
Andres E, Loukili NH, Noel E, Maloisel F, Vinzio S, Kaltenbach G, et al. Effects of oral crystalline cyanocobalamin 1000mg/day in the treatment of pernicious anemia: An open-label prospective study in ten patients. *Curr Ther Res* 2005; 66:13-22.
Andres E, Serraj K, Federici L, et al. Efficacité au long cours d'un traitement par cyanocobalamine administrée par voie orale dans le cadre des carences en vitamine B12: etude de 22 cas. *Rev Med Interne* 2007; 28 : Suppl 1: 49.
Berlin H, Berlin R, Brante E. Oral treatment of pernicious anemia with high doses of vitamin B12 without intrinsic factor. *Acta Med Scand.* 1968; 184: 247-58.
Bolaman Z, Kadikoylu G, Yulselen V, Yavasoglu I, Barutca S, Senturk T. Oral versus intramuscular cobalamin treatment in megaloblastic anemia: A single-center prospective, randomized, open-label study. *Clin Ther* 2003; 25: 3124-34.
Butler CC, Vidal-Alaball J, Cannings-John R, McCaddon A, Hood K, Papaioannou A et al. Oral vitamin B12 versus intramuscular vitamin B12 for vitamin B12 deficiency: a systematic review of randomized controlled trials. *Fam Pract* 2006; 23:279-85.
Dawson-Saunders B, Trapp RG. Basic and Clinical Biostatistics, 2 ed. Norwalk, CT, Lange Appleton, 1994.
DeSesso JM, Jacobson CF. Anatomical and physiological parameters affecting gastrointestinal absorption in humans and rats. *Food Chem Toxicol* 2001; 39: 209-28.
Ding X, Rath P, Angelo R, Stringfellow T, Flanders E, Dinh S, et al. Oral absorption enhancement of cromolyn sodium through noncovalent complexation. *Pharm Res* 2004; 21: 2196-206.
Doscherholmen A, Hagen PS. A dual mechanism of vitamin B12 plasma absorption. *J Clin Invest* 1955; 36: 1551-57.
Eussen SJPM, Ueland PM, Hiddink GJ, Schneede J, Blom HJ, Hofnagels WHL et al. Changes in markers of cobalamin status after cessation of oral B-vitamin supplements in elderly people with mild cobalamin deficiency. *Eu J Clin Nutr* 2008; 62: 1248-51.
Green R. Metabolite assays in cobalamin and folate deficiency. . In: Megaloblastic Anaemias: Bailliere's Clinical Haematology. SN. Wickramasinghe, Ed., 1995; 8: 533-66.
Herbert V. Staging B12 (cobalamin) status in vegetarians. *Am J Clin Nutr* 1994; 59 (suppl) : 1213S-22S.
Herrmann W, Obeid R, Schorr H, Geisel J. Functional vitamin B12 deficiency and determination of holotranscobalamin in populations at risk. *Clin Chem Lab Med* 2003; 41: 1478-88.
Hess S, Rotshild V, Hoffman A. Investigation of the enhancing mechanism of sodium *N*-[-(2-hydroxybenzoyl)amino]caprylate effect on the intestinal permeability of polar molecules utilizing a voltage clamp method. *Eu J Pharm Sci* 2005; 25: 307-312.
Karsdal MA. Byrjalsen I, Riis BJ, Christiansen C. Optimizing bioavailability of oral administration of small peptides through pharmacokinetic and pharmacodynamic parameters: The effect of water and timing of meal intake on oral delivery of Salmon Calcitonin. *BMC Clin Pharmacol* 2008: 8:5.
Kuzminski AM, Del Giacco EJ, Allen RH, Stabler SP, Lindenbaum J. Effective treatment of cobalamin deficiency with oral cobalamin. *Blood.* 1998; 92: 1191-98.
Mollin DL, Pitney WR, Baker SJ, Bradley JE. The plasma clearance and urinary excretion of parenterally administered 58Co B12. *Blood* 1956; 11: 31-43.

(Continued)

*Primary Examiner* — Elli Peselev
(74) *Attorney, Agent, or Firm* — Blank Rome LLP

(57) ABSTRACT

A novel method and composition for treating vitamin $B_{12}$ deficiency mammals that fail to respond to oral vitamin $B_{12}$ therapy.

29 Claims, 1 Drawing Sheet

OTHER PUBLICATIONS

Mollin DL, Ross GIM. Vitamin B12 concentrations of serum and urine in the first 72 hours after intramuscular injections of the vitamin. *J Clin Path* 1953; 6: 54-61.

Ross GIM, Mollin DL, Cox EV, Ungley CC. Hematologic responses and concentration of vitamin B12 in serum and urine following oral administration of vitamin B12 without intrinsic factor. *Blood* 1954; 9: 473-88.

Schilling RF. Pernicious Anemia. *JAMA* 1985; 253;94.

Arbit Ehud, et al., Oral Heparin: status review, Thrombosis Journal, Biomed Central, London, vol. 4, No. 1, May 10, 2006, p. 6.

Database Biosis, Biosciences Information Service, Philadelphia, PA, US: Dec. 23, Studies on gastrointestinal absorption enhancement effect and mechanism of sodium N-(-(2-hydroxybenzyl)amino) caprylate to insulin solution and Yaoxue Xuebao, vol. 38, No. 12, Dec. 2003, pp. 953-956.

Majuru S, Oral Delivery Advances in the Oral Delivery of Heparin From Solid Dosage Forms Using Emisphere's Eligen Oral Drug Delivery Technology, Drug Delivery Technology, vol. 4, No. 8, 1 Jan. 2004, pp. 85-89.

Malkov Dmitry, et al., Oral Delivery of insulin with eligen (R) technology: Mechanistic Studies, Current Drug Delivery, vol. 2, No. 2, Apr. 2005, pp. 191-197.

Stabler SP, Allen RH, Savage DD, Lindenbaum J. Clinical spectrum and diagnosis of cobalamin deficiency. Blood 1990; 76:871-81.

European Supplemental Search Report in EP 08844673.7 (dated Oct. 26, 2010).

Jun. 17, 2011 Email from Lance Liu to Jay Lessler.

Butler et al., Oral versus intramuscular cobalamin treatment in megaloblastic anemia: A single-center prospective, randomized, open-label study. *Clin Ther* 2003; 25; 3124-34.

Carmel, et al., Efficacy and safety of fortification and supplementation with vitamin B12: Biochemical and physiological effects, Food and Nutrition Bulletin, vol. 29, No. 2 (supplement) (2008), The United Nations University, S177-S187.

Hoey, et al., Studies of biomarker responses to intervention with vitamin B-12: a systematic review of randomized controlled trials, Am. J. Clin. Nutr. 2009, 89 (suppl):1981S-96S.

Hvas, et al., Diagnosis and treatment of vitamin B12 deficiency. An update, Haematologica 2006; 91:1506-1512.

Kaltenbach, et al., Reponse precoce au traitement oral par vitamine B12 Chez de sujets ages hypovitaminiques, Ann. Med. Interne, 2003, 154, No. 2, pp. 91-95.

Emails from Lance Liu entitled "Allegation of your violation of 37 C.F.R. 1.56".

Clarissa Kripke, M.D., Is Oral Vitamin $B_{12}$ as Effective as Intramuscular Injection?, *Am Fam Physician*. Jan. 1, 2006;73(1):65.

Jun. 16, 2011 Email from Lance Liu to Jay Lessler.

* cited by examiner

METHOD OF TREATING VITAMIN B12 DEFICIENCY

CROSS-REFERENCE TO PRIOR APPLICATIONS

This is a Non Provisional U.S. Application of three provisional applications, claiming the benefit of U.S. Provisional Application No. 60/984,898, filed Nov. 2, 2007; U.S. Provisional Application No. 61/020,108 filed on Jan. 9, 2008; and US Provisional Application No. 61/083,566 filed on Jul. 25, 2008.

FIELD OF THE INVENTION

The present invention relates generally to methods of treating vitamin $B_{12}$ deficiency and pharmaceutical compositions for such treatment.

BACKGROUND OF THE INVENTION

Vitamin $B_{12}$ is important for the normal functioning of the brain and nervous system and for the formation of blood. It is involved in the metabolism of every cell of the body, especially affecting the DNA synthesis and regulation but also fatty acid synthesis and energy production. Its effects are still not completely known.

Cyanocobalamin is the most stable and widely used form of vitamin $B_{12}$. It is bound to plasma proteins and stored in the liver. Vitamin $B_{12}$ is excreted in the bile and undergoes some enterohepatic recycling. Absorbed vitamin $B_{12}$ is transported via specific $B_{12}$ binding proteins, transcobalamin I and II, to the various tissues. The liver is the main organ for vitamin $B_{12}$ storage.

Vitamin $B_{12}$ deficiency can potentially cause severe and irreversible damage, especially to the brain and nervous system. Oral tablets containing vitamin $B_{12}$ have been developed to treat vitamin $B_{12}$ deficiency. However, many patients with vitamin $B_{12}$ deficiency do not respond to oral vitamin $B_{12}$ treatment. There is a need to develop a treatment for these patients.

BRIEF SUMMARY OF THE INVENTION

One aspect of the invention is directed to a method for treating vitamin $B_{12}$ deficiency in a subject, comprising the steps of (a) preparing a pharmaceutical composition for oral administration containing (1) vitamin $B_{12}$ and (2) at least one substance selected from the group consisting of N-[8-(2-hydroxybenzoyl)amino]caprylic acid and its pharmaceutically acceptable salts; and (b) administering the pharmaceutical composition to the subject to effectively treat said vitamin $B_{12}$ deficiency.

Another aspect of the invention is directed to a pharmaceutical composition for treating vitamin $B_{12}$ deficiency in a subject, comprising (1) vitamin $B_{12}$ and (2) at least one substance selected from the group consisting of N-[8-(2-hydroxybenzoyl)amino]caprylic acid and its pharmaceutically acceptable salts; wherein said subject had failed to respond to existing oral vitamin $B_{12}$ treatment.

The contents of the patents and publications cited herein and the contents of these documents cited in these patents and publications are hereby incorporated herein by reference to the extent permitted.

DETAILED DESCRIPTION

Figure 1:
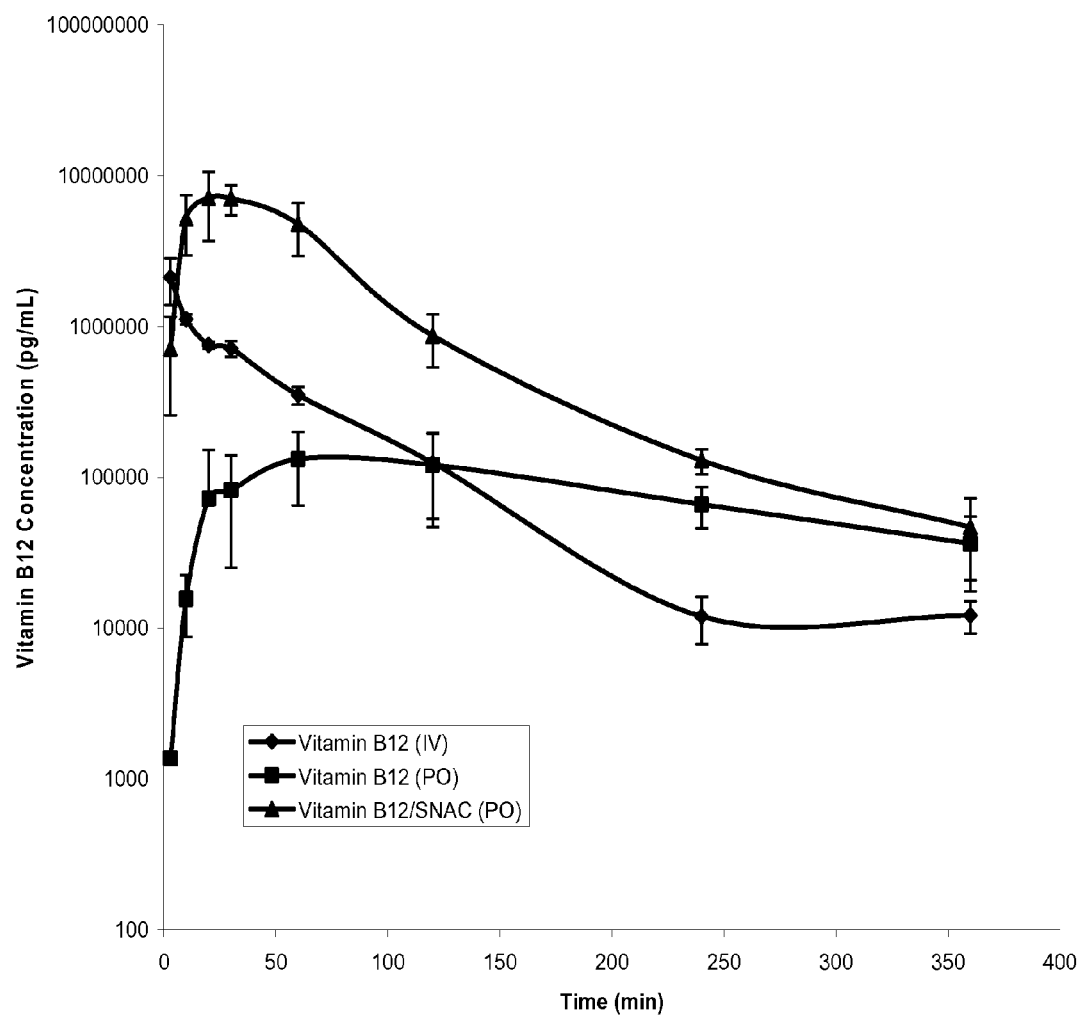
FIG. 1 is a graph of serum vitamin $B_{12}$ concentration as a function of time.

As used herein, the term "SNAC" means Sodium-N-salicyloyl-8-aminocaprylate, Monosodium 8-(N-salicyloylamino) octanoate, N-(salicyloyl)-8-aminooctanoic acid monosodium salt, monosodium N-{8-(2phenoxybenzoyl) amino}octanoate, E414 monosodium salt or sodium 8-[(2-hydroxybenzoyl)amino]octanoate. It has the structure

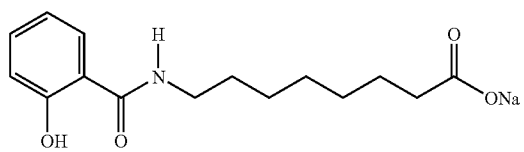

"N-[8-(2-hydroxybenzoyl) amino]caprylic acid" has an empirical formula $C_{15}H_{21}NO_4$ The term "Vitamin $B_{12}$" means any member of a group of cobalt-containing compounds known as cobalamins which include, but is not limited to cyanocobalamin, hydroxocobalamin, methylcobalamin, and 5-deoxyadenosylcobalamin.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms. The term "mammal" include human subjects.

The terms "carrier, excipient, emulsifier, stabilizer, sweetener, flavoring agent, diluent, coloring agent, solubilizing agent" are as defined in the Handbook of Pharmaceutical Excipients (fourth edition) by Raymond C. Rowe, Paul J. Sheskey and Paul J. Weller, the content of which is herein incorporated by reference.

The term "intrinsic factor protein" means is a glycoprotein produced by the parietal cells of the stomach. It is necessary for the absorption of vitamin $B_{12}$ later on in the terminal ileum.

In a preferred embodiment, the treatment is directed to subjects that had failed to respond to existing oral vitamin $B_{12}$ treatment. Preferably, tablets are used for the treatment. Such tablets contain from about 0.01 mg to about 25 mg of vitamin $B_{12}$ and from about 1 mg to about 600 mg of SNAC each, preferably from about 0.02 mg to about 25 mg of vitamin $B_{12}$ and more preferably from about 0.1 mg to about 20 mg of vitamin $B_{12}$ and the most preferably from about 0.5 mg to 10 mg of vitamin $B_{12}$ and from about 10 mg to about 200 mg of SNAC in each tablet.

The preferred weight ratio of vitamin $B_{12}$ and SNAC in the tablet is from about 2:1 to about 1:700, more preferably from about 1:2 to about 1:600 or from about 1:3 to about 1:20 and the most preferably from about 1:4 to about 1:10.

In a preferred embodiment, the pharmaceutical composition is in the form of tablets. Preferably, each tablet contains from about 0.01 mg to about 25 mg of vitamin $B_{12}$ and from about 50 mg to about 600 mg of SNAC. More preferably, each tablet contains from about 0.02 mg to about 20 mg of vitamin $B_{12}$. More preferably, each tablet contains from about 0.1 mg to about 10 mg of vitamin $B_{12}$. The most preferably, each tablet contains about 15 to 20 mg of vitamin $B_{12}$ and about 50 to 100 mg of SNAC, or about 0.1 to 1.5 mg of vitamin $B_{12}$ and about 25 to 150 mg of SNAC.

In another preferred embodiment, the tablet further contains at least one of a carrier, excipient, emulsifier, stabilizer, sweetener, flavoring agent, diluent, coloring agent, solubilizing agent or combinations thereof.

In another preferred embodiment, the tablet optionally contains from about 1 to 25 mg of Capmul PG-8 and optionally contains from about 0.5 to 10 mg of providone. Preferably, Capmul PG-8 is in an amount from about 2 to 20 mg and Providone is in an amount from about 1 to 8 mg. Preferably, Capmul PG-8 is in an amount from about 5 to 15 mg and the Providone is in an amount from about 1.5 to 5 mg. More preferably, Capmul PG-8 is in an amount from about 5 to 10 mg and Providone is in an amount from about 1.5 to 5 mg.

Without intending to be bound by any particular theory of operation, it is believed that gastrointestinal absorption of vitamin $B_{12}$ depends on the presence of sufficient intrinsic factor protein, secreted from gastric parietal cells. The average diet supplies about 10 mcg/day of vitamin $B_{12}$ in a protein-bound form that is available for absorption after normal digestion. Vitamin $B_{12}$ is bound to intrinsic factor during transit through the stomach; separation occurs in the terminal ileum, and vitamin $B_{12}$ enters the mucosal cell for absorption via a receptor mediated process. It is then transported by the transcobalamin binding proteins. A small amount (approximately 1% of the total amount ingested) is absorbed by simple diffusion, but this mechanism is adequate only with very large doses. It is also believed that SNAC will allow $B_{12}$ to bypass its usual receptor mediated process.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using concentrations, amounts, contents, carbon numbers, and properties that are outside of the range or different from a single value, will achieve the desired result, namely, effective treatment of a subject with vitamin $B_{12}$ deficiency which failed to respond to existing oral vitamin $B_{12}$ tablets as well as pharmaceutical compositions for such treatment.

Example 1

Preparation of
N-[8-(2-hydroxybenzoyl)amino]caprylic Acid and SNAC

The preparation method for N-[8-(2-hydroxybenzoyl)amino]caprylic acid and SNAC involves the following steps: The starting material is salicylamide, which is converted to form Carsalam. The second step involves the alkylation of Carsalam. The penultimate step is a hydrolysis to cleave the ethyl protection group at the end of the alkyl chain and spring open the heterocyclic ring forming the free acid of SNAC. In the final step, the sodium salt of the SNAC free acid is formed by reaction with a 1% excess stoichiometric amount of sodium hydroxide base. Upon cooling the precipitated product is isolated by centrifugation and vacuum dried prior to packaging. The in-process controls for the synthetic scheme are given in Table I.

TABLE I

In-process controls for SNAC Manufacturing Process.

| Step | Reaction | Desired Product | Specification | In-Process Control |
|---|---|---|---|---|
| 1 | Carsalam | Carsalam | <10% salicylamide | HPLC |
| 2 | Alkylation | Alkylated Carsalam | <8% Carsalam | HPLC |
| 3 | Hydrolysis | SNAC Free acid | <0.5% | LOD |
| 4 | Sodium Salt | SNAC Sodium salt | 95-105% | HPLC |

Example 2

Preparation of Vitamin $B_{12}$ Tablets

The tablet die and punches are checked to ensure that they are clean and that their surfaces are dusted with magnesium stearate powder. Vitamin $B_{12}$, SNAC, carrier, excipient, emulsifier, stabilizer, sweetener, flavoring agent, diluent, coloring agent, solubilizing agent are screened through a #35 sieve and transferred into a sealed containers. 50 mg of Vitamin $B_{12}$ is weighed and mixed thoroughly with 11 grams of a carrier, excipient, emulsifier, stabilizer, sweetener, flavoring agent, diluent, coloring agent and/or solubilizing agent. 100 vitamin $B_{12}$ tablets are made, with each tablet containing 0.5 mg of Vitamin $B_{12}$ and 110 mg of a carrier, excipient, emulsifier, stabilizer, sweetener, flavoring agent, diluent, coloring agent and/or solubilizing agent. These tablets are used as a control.

Example 3

Preparation of Vitamin $B_{12}$ and SNAC Tablets 50 mg of Vitamin $B_{12}$, 1 gram of SNAC are weighed and thoroughly mixed with 10 grams of a carrier, excipient, emulsifier, stabilizer, sweetener, flavoring agent, diluent, coloring agent and/or solubilizing agent. 100 vitamin $B_{12}$ tablets are made, with each tablet containing 0.5 mg of Vitamin $B_{12}$. 10 mg of SNAC and 100 mg of a carrier, excipient, emulsifier, stabilizer, sweetener, flavoring agent, diluent, coloring agent and/or solubilizing agent. The process is repeated to make tablet batches containing 1.0 mg, 0.8 mg, 0.6 mg, 0.4 mg and 0.2 of Vitamin $B_{12}$, respectively. These tablets have the following specifications for release of SNAC component:

| Tests | Specification | Analytical Method |
|---|---|---|
| Appearance | White to light-tan powder with pink hue | AM001 |
| Identification | | |
| Test for Sodium | Confirms presence of Sodium | USP <191> |
| FTIR | Conforms to reference standard | USP <197K> |

-continued

| Tests | Specification | Analytical Method |
|---|---|---|
| Melting Range/ Temperature | 193-203° C. with a range not to exceed 5° C. | USP <741> |
| Water Content | NMT 3.0% | USP <921> Method I |
| Heavy Metals | <20 ppm | USP <231> Method II |
| Sodium Content | 6.9 to 8.4% | AM017 |
| Residual Solvents | | |
| Ethanol | Less than 4000 ppm | AM008 |
| Heptane | Less than 500 ppm | AM008 |
| Assay as SNAC Sodium salt (As Is) | 90.0-110.0% w/w | AM016 |

Example 4

Preparation of Tablets for Testing on Rats

Tablets with four types of different ingredients were made as follows: (1) 8.8 mg of vitamin $B_{12}$, 35 mg of SNAC were weighed, thoroughly mixed and made into a tablet for dosing on rat; (2) 8.8 mg of vitamin $B_{12}$, 35 mg of SNAC and 5 mg of Capmul PG-8 were weighed, thoroughly mixed and made into a tablet; (3) 8.8 mg of vitamin $B_{12}$, 35 mg of SNAC and 0.9 mg of Providone were weighed, thoroughly mixed and made into a tablet. Each of the four processes was repeated to produce more tablets.

Example 5

Dosing Sprague-Dawley Rats

Male Sprague-Dawley rats (325-350 g) were dosed with vitamin $B_{12}$ intravenously (0.5 mg/kg) alone, or orally with the tablets made in Example 4 at a dose of 50 mg/kg vitamin $B_{12}$ alone or in combination with SNAC at 200 mg/kg. Blood samples were collected at 0, 3, 10, 20, 30, 60, 120, 240 and 360 minutes post dosing. Plasma samples were analyzed for B12 by RIA. The model independent PK metrics obtained following B12-SNAC combination were compared to those obtained following B12 alone. The testing results are shown in Table 1.

TABLE 1

Comparative Testing Results for Vitamin $B_{12}$ Absorption

| Group (N = 5) | Cmax (ug/mL) | | Tmax (min) | | AUC (ug * min/mL) | | Mean Bio-availability % |
|---|---|---|---|---|---|---|---|
| | Mean | S.D | Mean | S.D | Mean | S.D | |
| 0.5 mg/kg Vitamin $B_{12}$ (IV) | 2.15 | 0.64 | 4.4 | 3.13 | 65.84 | 11 | |
| 50 mg/kg Vitamin $B_{12}$ alone (PO) | 0.14 | 0.07 | 52 | 17.9 | 28.72 | 13 | 0.42 |
| 50 mg/kg Vitamin $B_{12}$ + 200 mg/kg SNAC (PO) | 7.99 | 2.41 | 24 | 5.48 | 522.37 | 179 | 7.93 |

Example 6

Preparation of Tablets for Testing on Human Subjects

Tablets were made from Cyanocobalamin, SNAC, Kollidon 90F, Anhydrous Emcompress USP/EP and Magnesium Stearate, NF/BP/EP/JP. Each tablet contains the followings:

| Ingredients | mg/tablet |
|---|---|
| Cyanocobalamin, USP (Intragranular) | 5.00 |
| SNAC (Intragranular) | 100.00 |
| Kollidon 90F, NF/EP/JP (Providone K90; Intragranular) | 2.00 |
| Anhydrous Emcompress USP/EP (Diabasic Calcium Phosphate, Anhydrous; Intragranular) | 70.00 |
| Anhydrous Emcompress USP/EP (Diabasic Calcium Phosphate, Anhydrous; Extragranular) | 21.00 |
| Magnesium Stearate, NF/BP/EP/JP (extragranular) | 2.00 |
| Total Weight | 200.0 |

Example 7

Dosing Human Subjects

Sixteen healthy male subjects were randomized to receive one of the following treatments:
(1) Treatment B: a single oral dose of cyanocobalamin/ SNAC (5 mg cyanocobalamin/100 mg SNAC) administered in the fasted state as a tablet. (6 subjects);
(2) Treatment C: a single oral dose of cyanocobalamin alone (5 mg cyanocobalamin, VitaLabs, commercial) administered in the fasted state as a tablet. (6 subjects).
(3) Treatment D: a single intravenous dose of cyanocobalamin (1 mg cyanocobalamin) administered in the fasted state. (4 subjects). Each subject received a 1 mL intravenous injection of a 1 mg/mL (1000 μg/mL) solution resulting in a total dose of 1 mg cyanocobalamin.

The subjects were fasted overnight prior to dosing and had no liquids (including water) consumption for at least one hour before and after dosing. The oral forms of cyanocobalamin/ SNAC tablets were administered in a single dose as tablets with 50 mL of plain water. Twenty-five blood samples were drawn for cyanocobalamin analyses at the following time points: within 30 minutes pre-dose and at Minutes 2, 5, 10, 20, 30, 40, 50, and at Hours 1, 1.5, 2, 3, 4, 5, 6, 7, 8, 9, 10, 11, 12, 14, 16, 20 and 24 post-dose.

Pharmacokinetic metrics was obtained following a model independent pharmacokinetic analysis of individual cyanocobalamin concentrations. Descriptive statistics was used to summarize the results.

Following 1 tablet of 5 mg B12/100 mg SNAC mean B12 peak concentration is 12847±6613 μg/mL and occur within 1 hour post dose (mean tmax of 0.50±0.21 hours). Mean AUClast (0-24) value is 54618±16392 hr*pg/mL. The percent coefficient of variation (% CV) is 51.5% for Cmax and 30.0% for AUC.

Following a single oral dose of cyanocobalamin alone (5 mg cyanocobalamin, VitaLabs, commercial) mean B12 peak concentration is 1239±450 μg/mL and occur between 3 to 10 hours post-dose (mean tmax of 6.8±3.2 hours). Mean AUClast (0-24) value is 23131±8343 hr*pg/mL. The percent coefficient of variation (% CV) is 36.3% for Cmax and 36.1% for AUC.

Following a single intravenous dose of cyanocobalamin (1 mg cyanocobalamin) administered in the fasted state (4 subjects). Mean B12 peak concentration is 221287±80248 pg/mL and mean AUClast (0-24) value is 215391±44602 hr*pg/mL. The percent coefficient of variation (% CV) is 36.3% for Cmax and 20.7% for AUC.

The mean bioavailability of 1 tablet of 5 mg vitamin B12 alone, 1 tablet of 5 mg vitamin B12/100 mg SNAC, and 2 tablets of 5 mg vitamin B12/100 mg SNAC are 2.15±0.77%, 5.07±1.52, and 5.92±3.05%, respectively. (Note: 2 tablets of 5 mg vitamin B12/100 mg SNAC were dosed previously in a pilot arm are designated Treatment A).

The mean tmax of 1 tablet of 5 mg vitamin B12 alone, 1 tablet of 5 mg vitamin B12/100 mg SNAC, and 2 tablets of 5 mg vitamin B12/100 mg SNAC are 6.8±3.2 hours, 0.50±0.21 hours, and 0.54±0.32 hours, respectively.

No adverse events were observed during the given treatments. All formulations appear to be safe and well tolerated.

It was found surprisingly that the extent of B12 absorption, measured as Cmax and AUC, was significantly enhanced by the administration of the cyanocobalamin/SNAC combination. Vitamin B12 bioavailability was ~240% greater for the 1 tablet of 5 mg B12/100 mg SNAC compared to 5 mg B12 commercial formulation. Mean peak B12 concentrations following B12 commercial oral formulation occurred significantly later compared to that following the B12/SNAC combinations likely due to a different site of absorption between the two oral formulations. This is consistent with literature data describing intestinal absorption of B12 occurring in the distal section of the gastrointestinal tract in the absence of the carrier.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:

1. A method for treating vitamin $B_{12}$ deficiency in a subject in need thereof, comprising orally administering to the subject a pharmaceutical composition comprising (1) vitamin $B_{12}$ and (2) a compound selected from N-[8-(2-hydroxybenzoyl)amino]caprylic acid and pharmaceutically acceptable salts thereof, wherein the pharmaceutical composition comprises an effective amount of the compound such that, upon oral administration of the pharmaceutical composition, the $T_{max}$ of the vitamin $B_{12}$ is decreased.

2. The method of claim 1, wherein said subject has failed to respond to existing oral vitamin $B_{12}$ treatment.

3. The method of claim 1, wherein said pharmaceutical composition is a tablet.

4. The method of claim 3, wherein said tablet comprises from about 0.01 mg to about 25 mg of vitamin $B_{12}$ and from about 1 mg to about 600 mg of monosodium N-[8-(2-hydroxybenzoyl)amino]caprylate.

5. The method of claim 3, wherein said tablet comprises from about 0.02 mg to about 25 mg of vitamin $B_{12}$.

6. The method of claim 3, wherein said tablet comprises from about 0.1 mg to about 20 mg of vitamin $B_{12}$.

7. The method of claim 3, wherein said tablet comprises about 0.5 mg of vitamin $B_{12}$ and about 17.5 mg of monosodium N-[8-(2-hydroxybenzoyl) amino]caprylate.

8. The method of claim 1, wherein said pharmaceutical composition has a weight ratio of vitamin $B_{12}$ to monosodium N-[8-(2-hydroxybenzoyl) amino]caprylate of from about 2:1 to about 1:700.

9. The method of claim 8, wherein said weight ratio is from about 1:2 to about 1:600.

10. The method of claim 8, wherein said weight ratio is from about 1:3 to about 1:20.

11. The method of claim 8, wherein said weight ratio is about 1:4.

12. The method of claim 8, wherein said weight ratio is from about 1:500 to about 1:700.

13. The method of claim 3, wherein said pharmaceutical composition further comprises at least one of a carrier, excipient, emulsifier, stabilizer, sweetener, flavoring agent, diluent, coloring agent, solubilizing agent or combinations thereof.

14. An oral pharmaceutical composition comprising (1) vitamin $B_{12}$ and (2) an effective amount of a compound selected from N-[8-(2-hydroxybenzoyl)amino]caprylic acid and pharmaceutically acceptable salts thereof such that, upon oral administration of the pharmaceutical composition, the $T_{max}$ of the vitamin $B_{12}$ is decreased.

15. The pharmaceutical composition of claim 14, wherein said pharmaceutical composition is in the form of a tablet.

16. The pharmaceutical composition of claim 15, wherein said tablet comprises from about 0.01 mg to about 25 mg of vitamin $B_{12}$ and from about 50 mg to about 600 mg of monosodium N-[8-(2-hydroxybenzoyl)amino]caprylate.

17. The pharmaceutical composition of claim 15, wherein said tablet comprises from about 0.02 mg to about 20 mg of vitamin $B_{12}$.

18. The pharmaceutical composition of claim 15, wherein said tablet comprises from about 0.1 mg to about 10 mg of vitamin $B_{12}$.

19. The pharmaceutical composition of claim 15, wherein said tablet comprises about 1 to 15 mg of vitamin $B_{12}$ and about 50 to 200 mg of monosodium N-[8-(2-hydroxybenzoyl)amino]caprylate.

20. The pharmaceutical composition of claim 14, further comprising at least one of a carrier, excipient, emulsifier, stabilizer, sweetener, flavoring agent, diluent, coloring agent, solubilizing agent or combinations thereof.

21. An oral pharmaceutical composition comprising 0.5 to 10 mg of vitamin $B_{12}$ and from 10 to 200 mg of monosodium N-[8-(2-hydroxybenzoyl)amino]caprylate, wherein the pharmaceutical composition comprises an effective amount of monosodium N-[8-(2-hydroxybenzoyl)amino]caprylate such that, upon oral administration of the pharmaceutical composition, the $T_{max}$ of the vitamin $B_{12}$ is decreased.

22. The oral pharmaceutical composition of claim 21, wherein the pharmaceutical composition is a tablet.

23. A method of treating vitamin $B_{12}$ deficiency in a subject in need thereof, the method comprising orally administering to the subject a pharmaceutical composition comprising 0.5 to 10 mg of vitamin $B_{12}$ and from 10 to 200 mg of monosodium N-[8-(2-hydroxybenzoyl)amino]caprylate, wherein the pharmaceutical composition comprises an effective amount of monosodium N-[8-(2-hydroxybenzoyl)amino]caprylate such that, upon oral administration of the pharmaceutical composition, the $T_{max}$ of the vitamin $B_{12}$ is decreased.

24. The method of claim 23, wherein the subject is a human.

25. The method of claim 1, wherein, upon oral administration, the pharmaceutical composition exhibits a mean $T_{max}$ for the vitamin $B_{12}$ of 0.50 hours.

26. The pharmaceutical composition of claim 14, wherein the pharmaceutical composition exhibits a mean $T_{max}$ for the vitamin $B_{12}$ of 0.50 hours.

27. The pharmaceutical composition of claim 21, wherein, upon oral administration, the pharmaceutical composition exhibits a mean $T_{max}$ for the vitamin $B_{12}$ of 0.50 hours.

28. The method of claim 23, wherein the pharmaceutical composition exhibits a mean $T_{max}$ for the vitamin $B_{12}$ of 0.50 hours.

29. The oral pharmaceutical composition of claim 14, wherein the oral pharmaceutical composition comprises about 0.1 to 1.5 mg of vitamin $B_{12}$ and from 25 to 100 mg of monosodium N-[8-(2-hydroxybenzoyl)amino]caprylate.

* * * * *